(12) United States Patent
Saadat

(10) Patent No.: US 7,160,255 B2
(45) Date of Patent: Jan. 9, 2007

(54) METHOD AND DEVICE FOR SENSING AND MAPPING TEMPERATURE PROFILE OF A HOLLOW BODY ORGAN

(75) Inventor: Vahid Saadat, 12679 Kane Dr., Saratoga, CA (US) 95070

(73) Assignee: Vahid Saadat, Saratoga, CA (US)

( * ) Notice: Subject to any disclaimer, the term of this patent is extended or adjusted under 35 U.S.C. 154(b) by 0 days.

(21) Appl. No.: 10/452,409

(22) Filed: May 30, 2003

(65) Prior Publication Data

US 2004/0059235 A1    Mar. 25, 2004

Related U.S. Application Data

(63) Continuation-in-part of application No. 09/904,212, filed on Jul. 12, 2001, now abandoned, and a continuation-in-part of application No. 09/904,024, filed on Jul. 12, 2001, now abandoned.

(51) Int. Cl.
   *A61B 5/00* (2006.01)
   *A61M 25/00* (2006.01)
   *A61B 5/05* (2006.01)

(52) U.S. Cl. .................. 600/549; 600/585; 600/547

(58) Field of Classification Search ............ 600/373, 600/381, 433–435, 474, 547, 549, 585, 38; 604/528, 530; 374/148, 166, 179
   See application file for complete search history.

(56) References Cited

U.S. PATENT DOCUMENTS

| | | | |
|---|---|---|---|
| 4,215,275 A | 7/1980 | Wickersheim | |
| 4,301,023 A | 11/1981 | Schuberth et al. | |
| 4,411,266 A * | 10/1983 | Cosman | 606/49 |
| RE32,204 E | 7/1986 | Halvorsen | |
| 4,699,147 A | 10/1987 | Chilson et al. | |
| 4,777,955 A | 10/1988 | Brayton et al. | |
| 4,862,887 A | 9/1989 | Weber et al. | |
| 4,883,459 A | 11/1989 | Calderon | |
| 4,952,033 A | 8/1990 | Davis | |
| 4,958,642 A | 9/1990 | Christian et al. | |
| 4,995,398 A | 2/1991 | Turnidge | |
| 5,054,501 A | 10/1991 | Chuttani et al. | |

(Continued)

FOREIGN PATENT DOCUMENTS

WO    WO 97/10748 A1    3/1997

(Continued)

OTHER PUBLICATIONS

Pasterkamp, G. et al. (Jul. 2000). "Techniques Characterizing the Coronary Atherosclerotic Plaque: Influence on Clinical Decision Making?" *J. Am. Coll. Cardiol.* 36(1):13-21.

(Continued)

*Primary Examiner*—Charles A Marmor, II
(74) *Attorney, Agent, or Firm*—Levine Bagade Han LLP

(57) ABSTRACT

A method and device for sensing the temperature profile of a hollow body organ includes a catheter and a hollow guidewire carrying a thermal sensor. The guidewire is configured to displace the thermal sensor radially relative to the catheter when unconstrained and can be rotated about the longitudinal axis of the catheter. When constrained within the catheter, the guidewire can be advanced to a region of interest in hollow body organ. The catheter can be withdrawn, leaving the guidewire in place in an expanded configuration wherein the thermal sensor contacts the inner wall of the hollow body organ. The guidewire is moveable to sense the temperature at multiple locations. The thermal sensor can be replaced with an electrode for sensing the impedance profile of the hollow body organ.

41 Claims, 10 Drawing Sheets

U.S. PATENT DOCUMENTS

| | | | |
|---|---|---|---|
| 5,069,226 A | 12/1991 | Yamauchi et al. | |
| 5,124,819 A | 6/1992 | Davis | |
| 5,178,159 A | 1/1993 | Christian | |
| 5,237,996 A | 8/1993 | Waldman et al. | |
| 5,279,299 A | 1/1994 | Imran | |
| 5,304,194 A | 4/1994 | Chee et al. | |
| 5,342,300 A | 8/1994 | Stefanadis et al. | |
| 5,623,940 A | 4/1997 | Daikuzono | |
| 5,657,764 A | 8/1997 | Coulter et al. | |
| RE35,648 E | 11/1997 | Tenerz et al. | |
| 5,701,905 A | 12/1997 | Esch | |
| 5,730,741 A | 3/1998 | Horzewski et al. | |
| 5,733,739 A | 3/1998 | Zakim et al. | |
| 5,741,214 A | 4/1998 | Ouchi et al. | |
| 5,769,846 A | 6/1998 | Edwards et al. | |
| 5,771,895 A | 6/1998 | Slager | |
| 5,782,741 A | 7/1998 | Bradshaw et al. | |
| 5,871,449 A | 2/1999 | Brown | |
| 5,910,101 A | 6/1999 | Andrews et al. | |
| 5,924,997 A | 7/1999 | Campbell | |
| 5,935,075 A | 8/1999 | Casscells et al. | |
| 5,938,624 A | 8/1999 | Akerfeldt et al. | |
| 5,980,563 A | 11/1999 | Tu et al. | |
| 5,989,242 A | 11/1999 | Saadat et al. | |
| 6,010,476 A | 1/2000 | Saadat | |
| 6,071,277 A | 6/2000 | Farley et al. | |
| 6,090,052 A | 7/2000 | Akerfeldt et al. | |
| 6,106,486 A | 8/2000 | Tenerz et al. | |
| 6,142,958 A | 11/2000 | Hammarstrom et al. | |
| 6,156,046 A | 12/2000 | Passafaro et al. | |
| 6,167,763 B1 | 1/2001 | Tenerz et al. | |
| 6,196,980 B1 | 3/2001 | Akerfeldt et al. | |
| 6,197,021 B1 | 3/2001 | Panescu et al. | |
| 6,245,026 B1 | 6/2001 | Campbell et al. | |
| 6,267,746 B1 | 7/2001 | Bumbalough | |
| 6,267,781 B1 | 7/2001 | Tu | |
| 6,312,425 B1 | 11/2001 | Simpson et al. | |
| 6,371,928 B1 | 4/2002 | Mcfann et al. | |
| 6,406,442 B1 | 6/2002 | McFann et al. | |
| 6,615,071 B1 * | 9/2003 | Casscells et al. | 600/474 |
| 2001/0053882 A1 | 12/2001 | Haddock et al. | |
| 2002/0067754 A1 | 6/2002 | Werneth | |
| 2003/0088187 A1 * | 5/2003 | Saadat et al. | 600/547 |

FOREIGN PATENT DOCUMENTS

| | | |
|---|---|---|
| WO | WO 00/27278 A1 | 5/2000 |
| WO | WO 01/74263 A1 | 10/2001 |

OTHER PUBLICATIONS

Stefanadis, C. et al. (Apr. 1999). "Thermal Heterogeneity Within Human Atherosclerotic Coronary Arteries Detected In Vivo," *Circulation* 99:1965-1971.

Bolz, Ray E. and Tuve, George L. (eds) (1973) Chapter 10 Transducers and Measurement Techniquest, *CRC Handbook of Tables for Applied Engineering Science*, 2nd edition, CRC Press, pp. 975-978.

* cited by examiner

METHOD AND DEVICE FOR SENSING AND MAPPING TEMPERATURE PROFILE OF A HOLLOW BODY ORGAN

CROSS-REFERENCE TO RELATED APPLICATIONS

This is a continuation-in-part of U.S. patent application Ser. No. 09/904,212 filed Jul. 12, 2001 (now abandoned) and is a continuation-in-part of U.S. patent application Ser. No. 09/904,024 also filed Jul. 12, 2001 (now abandoned), each of which is incorporated herein by reference in its entirety.

FIELD OF THE INVENTION

This invention relates generally to invasive medical devices and more particularly to methods and devices for sensing and mapping the temperature of the interior wall of a hollow body organ such as a blood vessel.

BACKGROUND OF THE INVENTION

Acute ischemic syndromes involving arterial blood vessels, such as myocardial infarction, or heart attack, and stroke, frequently occur when atherosclerotic plaque ruptures, triggering the formation of blood clots, or thrombosis. Plaque that is inflamed is particularly unstable and vulnerable to disruption, with potentially devastating consequences. Therefore, there is a strong need to detect and locate this type of plaque so that treatment can be initiated before the plaque undergoes disruption and induces subsequent life-threatening clotting.

Various procedures are known for detecting and locating plaque in a blood vessel. Angiography is one such procedure in which X-ray images of blood vessels are generated after a radiopaque dye is injected into the blood stream. This procedure is capable of locating plaque in an artery, but is not capable of revealing whether the plaque is the inflamed, unstable type.

Researchers, acting on the theory that inflammation is a factor in the development of atherosclerosis, have discovered that local variations of temperature along arterial walls can indicate the presence of inflamed plaque. The temperature at the site of inflamation, i.e., the unstable plaque, is elevated relative to adjacent plaque-free arterial walls.

Using a tiny thermal sensor at the end of a catheter, the temperature at multiple locations along an arterial wall were measured in people with and without atherosclerotic arteries. In people free of heart disease, the temperature was substantially homogeneous wherever measured: an average of 0.65 degrees F. above the oral temperature. In people with stable angina, the temperature of their plaques averaged 0.19 degrees F. above the temperature of their unaffected artery walls. The average temperature increase in people with unstable angina was 1.23 degrees F. The increase was 2.65 degrees F. in people who had just suffered a heart attack. Furthermore, temperature variation at different points at the plaque site itself was found to be greatest in people who had just had a heart attack. There was progressively less variation in people with unstable angina and stable angina.

The temperature heterogeneity discussed above can be exploited to detect and locate inflamed, unstable plaque through the use of cavity wall profiling apparatus. Typically, cavity wall profiling apparatus are comprised of temperature indicating probes such as thermocouples, thermistors, fluorescence lifetime measurement systems, resistance thermal devices and infrared measurement devices.

One problem with conventional cavity wall profiling apparatus is that they usually exert an undue amount of force on the region of interest. If the region of interest cannot withstand these forces, it may be damaged. The inside walls of a healthy human artery are vulnerable to such damage. Furthermore, if inflamed, unstable plaque is present it may be ruptured by such forces.

Another problem with conventional cavity wall profiling apparatus is that they can only measure the temperature at one specific location. In order to generate a map of the cavity temperature variation, one would need to move the temperature indicating probe from location to location. This can be very tedious, can increase the risk of damaging the vessel wall or rupturing vulnerable plaque, and may not resolve temporal characteristics of the profile with sufficient resolution. An array of probes could be employed but that could be very big and heavy.

SUMMARY OF THE INVENTION

According to one aspect of the invention, a device is provided for sensing the temperature profile of a hollow body organ. The device includes a catheter, a hollow guidewire, and a temperature sensor disposed on or within the guidewire. The guidewire has a relaxed configuration externally of the catheter that is formed to provide contact with the wall of the hollow body organ. The guidewire also has a contracted configuration internally of the catheter and is of a lesser diameter than the catheter.

According to another aspect of the invention, a method for sensing and mapping the temperature profile of a hollow body organ utilizes a catheter, a guidewire, and a thermal sensor disposed on or within the guidewire. The guidewire has a relaxed configuration externally of the catheter that is formed to provide contact with the wall of the hollow body organ. The guidewire also has a contracted configuration internally of the catheter and is of a lesser diameter than the catheter.

The device is used by contracting the guidewire elastically and constraining the guidewire within the catheter. The catheter and guidewire are advanced to a region of interest in a hollow body organ. The catheter is withdrawn to expose the distal portion of the guidewire in a relaxed configuration in contact with the hollow body organ. The guidewire is moved longitudinally and rotated, continuously or continually, to sense the temperature of the hollow body organ at multiple locations.

Further aspects and advantages of the present invention are apparent from the following description of a preferred embodiment referring to the drawings.

DETAILED DESCRIPTION OF THE INVENTION

Figure 1:
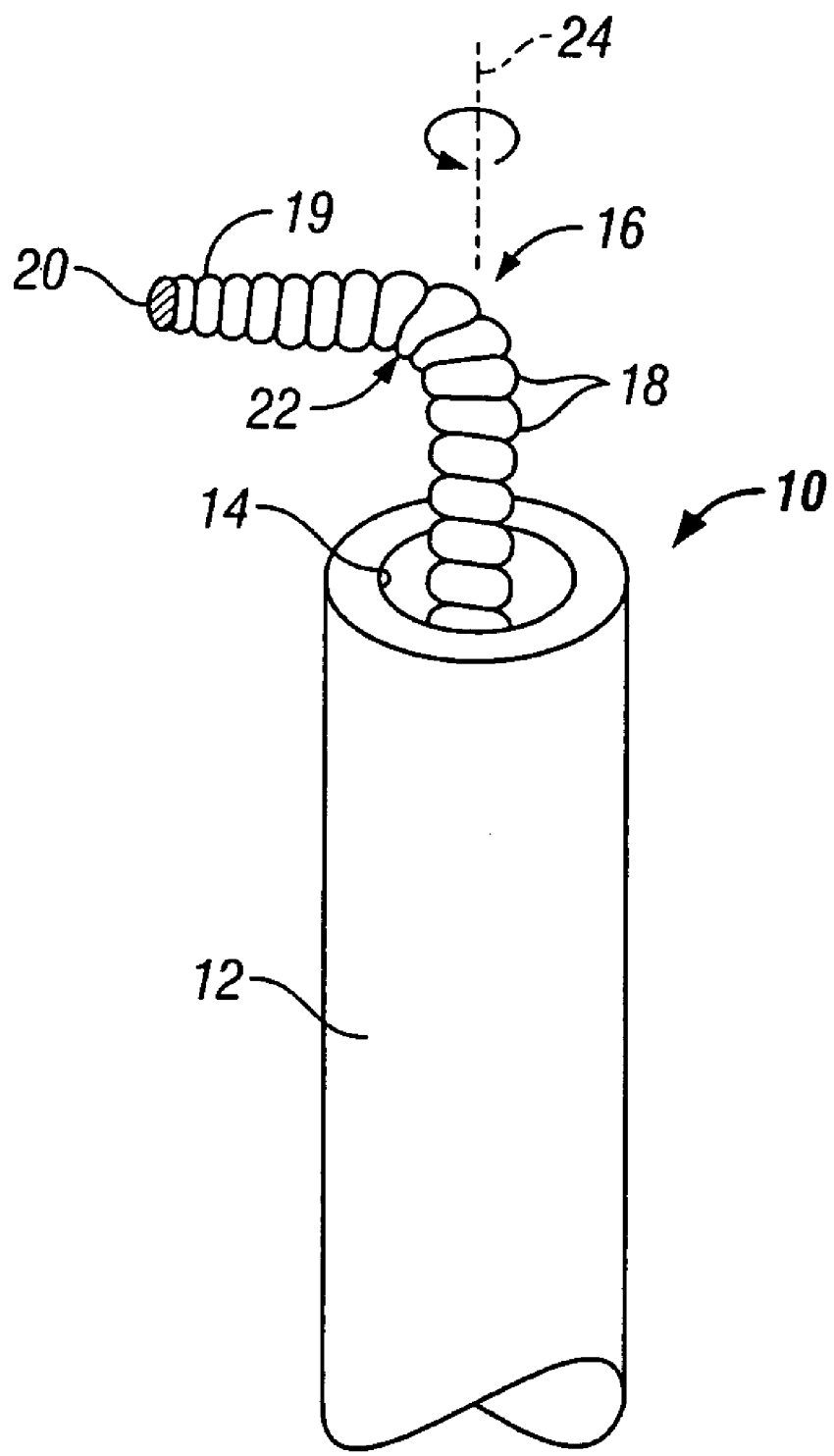
FIG. 1 is a perspective view of a preferred embodiment of the present invention.

FIG. 1 shows a device 10 for profiling the wall of a hollow body organ device 10 includes a lumened catheter 12 having a central lumen 14, a hollow guidewire 16 that defines a conduit comprising a tubular helix formed of metal wire 18 or the like in the shape of a coil defining a central lumen (not shown), and a thermal sensor 20 disposed at the terminal end of the distal portion of guidewire 16. Conventional conductors or other signal carrying structures (not shown) are provided to convey signals from the thermal sensor 20 along guidewire 16 and out of the proximal portion of guidewire 16 for connection to appropriate signal processing apparatus that converts the signals to a temperature indication. Thermal sensor 20 can be a thermocouple, a thermistor, or an infrared radiation sensor, for example, and is secured by appropriate mechanical or adhesive means to the terminal end of guidewire 16.

Hollow guidewire 16 is made of thin wire 18 wound, for example around a mandrel, into small helical coils of desired diameter that lie tightly adjacent one another to form a hollow tube having a central passageway or lumen therethrough. Guidewire 16 has an outer diameter somewhat less than the inner diameter of catheter 12 to permit guidewire 16 to slide freely within the lumen 14 of catheter 12. In addition, guidewire 16, in its relaxed configuration, is shaped in the form of a bend 22 at the distal portion thereof, the bend 22 being spaced from the terminal end of guidewire 16 at which thermal sensor 20 is disposed. Consequently, thermal sensor 20 is displaced radially from the longitudinal axis 24 of guidewire 16 and catheter 12 when guidewire 16 is in the relaxed, bent configuration. Through external manipulation, guidewire 16 in the relaxed, bent configuration can be made to rotate about axis 24, continuously or continually, depending on the response time for the sensor, thereby causing thermal sensor 20 to traverse a circumferential or helical path about axis 24 while providing temperature information. Guidewire 16 can be deformed elastically into a substantially straight configuration, i.e., without bend 22, under force. When the force is removed, guidewire 16 returns to the relaxed, bent configuration.

Guidewire 16 can be constructed of spring steel that can be deformed into a relatively straight configuration when withdrawn into catheter 12, but which springs back to its bent configuration when extruded from catheter 12 and released from constraint. Another way is to construct guidewire 16 of superelastic Nitinol and take advantage of the martensitic transformation properties of Nitinol. Guidewire 16 can be inserted into catheter 12 in its straight form and kept cool within the catheter by the injection of cold saline through catheter 12 and over guidewire 16. Upon release of guidewire 16 into the bloodstream, it will warm up and change to its austenite memory shape based on the well-known martensitic transformation by application of heat and putting the material through its transformation temperature.

Guidewire 16 can also be made out of a composite such as a Nitinol tube within the guidewire structure. In this fashion, the martensitic or superelastic properties of Nitinol can be combined with the spring steel characteristics of the spring and lead to a desirable composition. Other suitable materials for guidewire 16 include copper, constantin, chromel or alumel.

Figure 2:
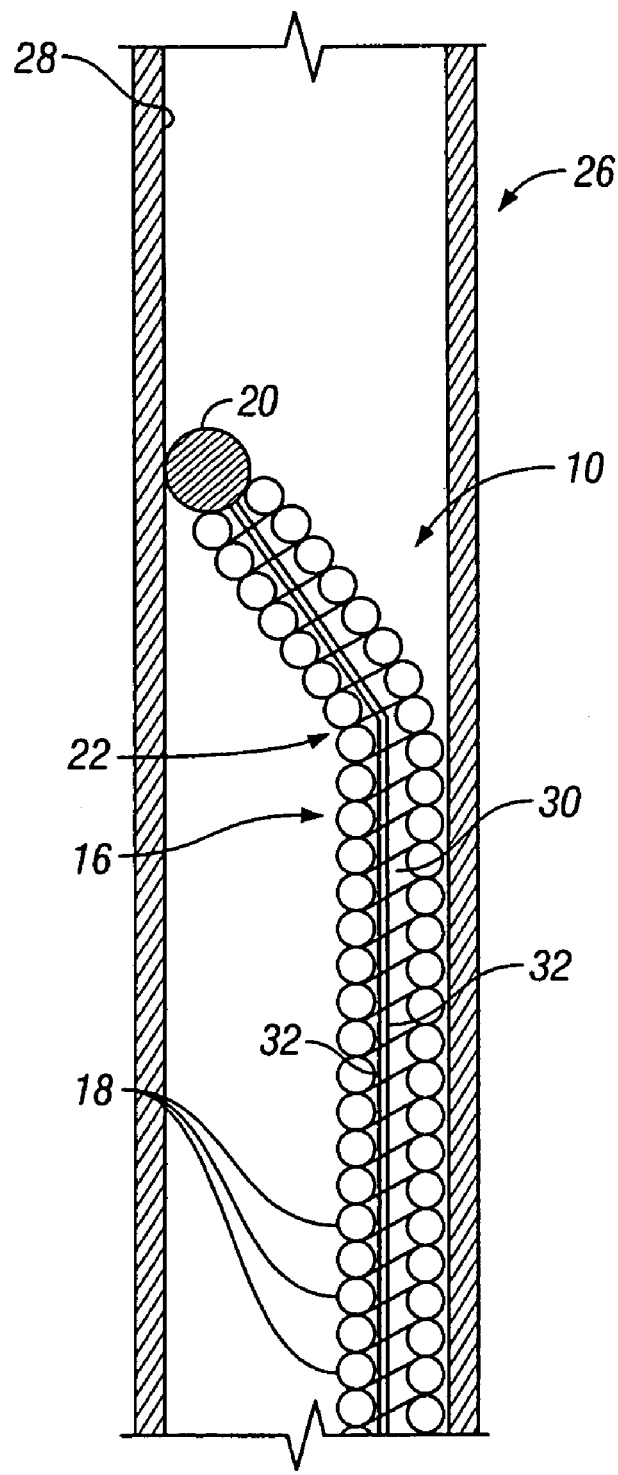
FIG. 2 is a longitudinal sectional view of an arterial hollow body organ in which the embodiment of FIG. 1, also shown in longitudinal section, is deployed.

FIG. 2 shows device 10 deployed in a hollow body organ comprising an arterial blood vessel 26 having an endothelium 28 forming the inner wall thereof. Only the distal portion of guidewire 16 that extends beyond catheter 12 is shown. Electrical conductor 32 extends through lumen 30 of guidewire 16. Conductor 32 is electrically insulated from the coils 18 of guidewire 16 so that guidewire 16 comprises one conductor and conductor 32 comprises another conductor or lead of the thermal sensor 20 which can be thermocouple or thermistor. The conductors conveys signals from the thermal sensor 20 to the proximal end of guidewire 16 for connection to appropriate signal processing apparatus that converts the received signals to a temperature indication.

In use, the guidewire 16 and thermal sensor 20 of the preferred embodiment of device 10, as shown in FIGS. 1 and 2, are inserted into the lumen 14 of catheter 12 from the proximal end. thereby constraining guidewire 16 in a substantially straight configuration with the thermal sensor 20 near the distal end of catheter 12. Using conventional percutaneous insertion techniques, access to the blood vessel 26 is obtained surgically. Catheter 12, with guidewire 16 and thermal sensor 20 disposed within, is advanced through the blood vessel 26 to the region of interest.

Catheter 12 is slowly withdrawn while guidewire 16 is secured against movement relative to the patient such that guidewire 16 emerges from the distal end of catheter 12 and reverts to the relaxed, bent configuration within the blood vessel 26. Guidewire 16 remains substantially fixed in the axial direction relative to the blood vessel 26 as catheter 12 is withdrawn, with the re-formed bent distal portion of guidewire 16 springing gently radially outwardly into contact with the vessel wall 28.

With guidewire 16 exposed and thermal sensor 20 lying in contact with the wall 28 of blood vessel 26, the thermal sensor 20 senses the localized temperature of the vessel wall 28 at the region where the thermal sensor 20 is situated. By slowly withdrawing guidewire 16 into catheter 12 while simultaneously rotating guidewire 16 about its longitudinal axis, thermal sensor 20 can be made to traverse a helical path around the inner wall 28 of the blood vessel 26, permitting temperature measurements to be taken at intervals of different regions of the vessel wall 28. Depending upon the response time of thermal sensor 20, rotation can be intermittent or continuous, as needed. By withdrawing and rotating the guidewire 16 at constant rates, the location of the thermal sensor 20 relative to the distal end of the catheter 12 can be determined as a function of time, so that a temperature profile of the blood vessel 26 can be mapped, provided the response time of the thermal sensor is relatively short.

Once the mapping is completed, the guidewire 16 is withdrawn fully into catheter 12, re-sheathed and constrained in a substantially straight configuration. Catheter 12 can then either be withdrawn from the blood vessel 26 or repositioned to another region of interest within the hollow body organ for further mapping of the temperature profile at that region.

Figure 3:
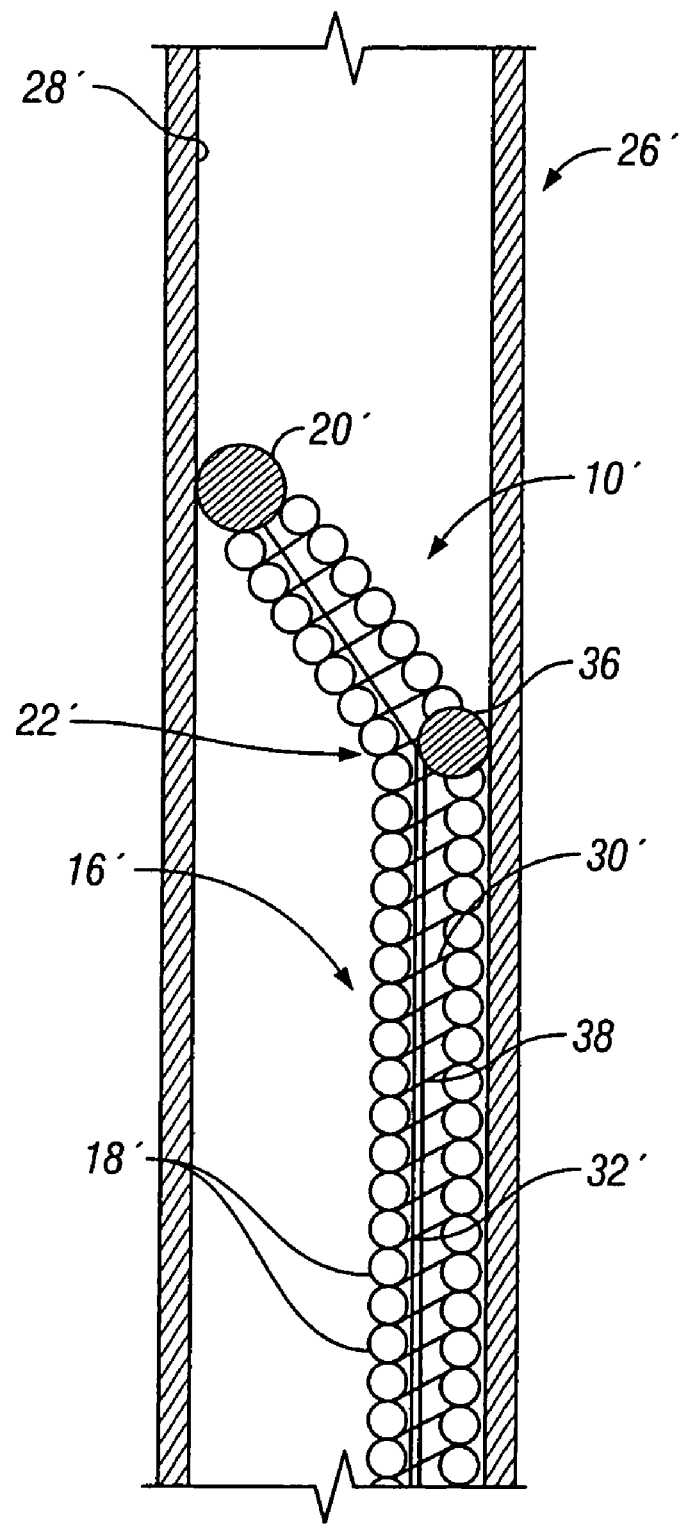
FIG. 3 is a longitudinal sectional view of an arterial hollow body organ in which another preferred embodiment of the present invention, also shown in longitudinal section, is deployed.

FIG. 3 shows a second preferred embodiment of a device 10' for profiling the wall of a hollow body organ. Device 10' can be deployed in a hollow body organ in a manner similar to the embodiment of device 10 shown in FIGS. 1 and 2 and described above with respect to structure and use. Components of device 10' that are similar in structure and function to corresponding components of device 10 of FIGS. 1 and 2 are designated by like prime numerals. The description of device 10 above applies also to device 10' unless described otherwise below.

Device 10' includes a second thermal sensor 36 disposed at the outside of bend 22' and exposed for contact with the inner wall 28' of vessel 26'. A second electrical conductor 38 is electrically insulated from the conductor 32' and from the wire 18' of guidewire 16' so that guidewire 16' comprises one conductor and conductor 38 comprises another conductor of the thermocouple or thermistor of thermal sensor 36 for conveying signals from the thermal sensor 36 to the proximal end of guidewire 16 for connection to appropriate signal processing apparatus that converts the signals to a temperature indication. Wire 18' of guidewire 16' is a conductor common to thermal sensors 20' and 36.

Device 10' of FIG. 3 can be used in a manner substantially similar to the manner of use described above with respect to device 10 of FIGS. 1 and 2, except that thermistors 20' and 36 simultaneously traverse intertwined helical paths in contact with the inner wall 28' of hollow body organ 26'. Consequently, the temperature profile of the inner wall 28' can be mapped more quickly because data can be gathered from different locations simultaneously.

Figure 4:
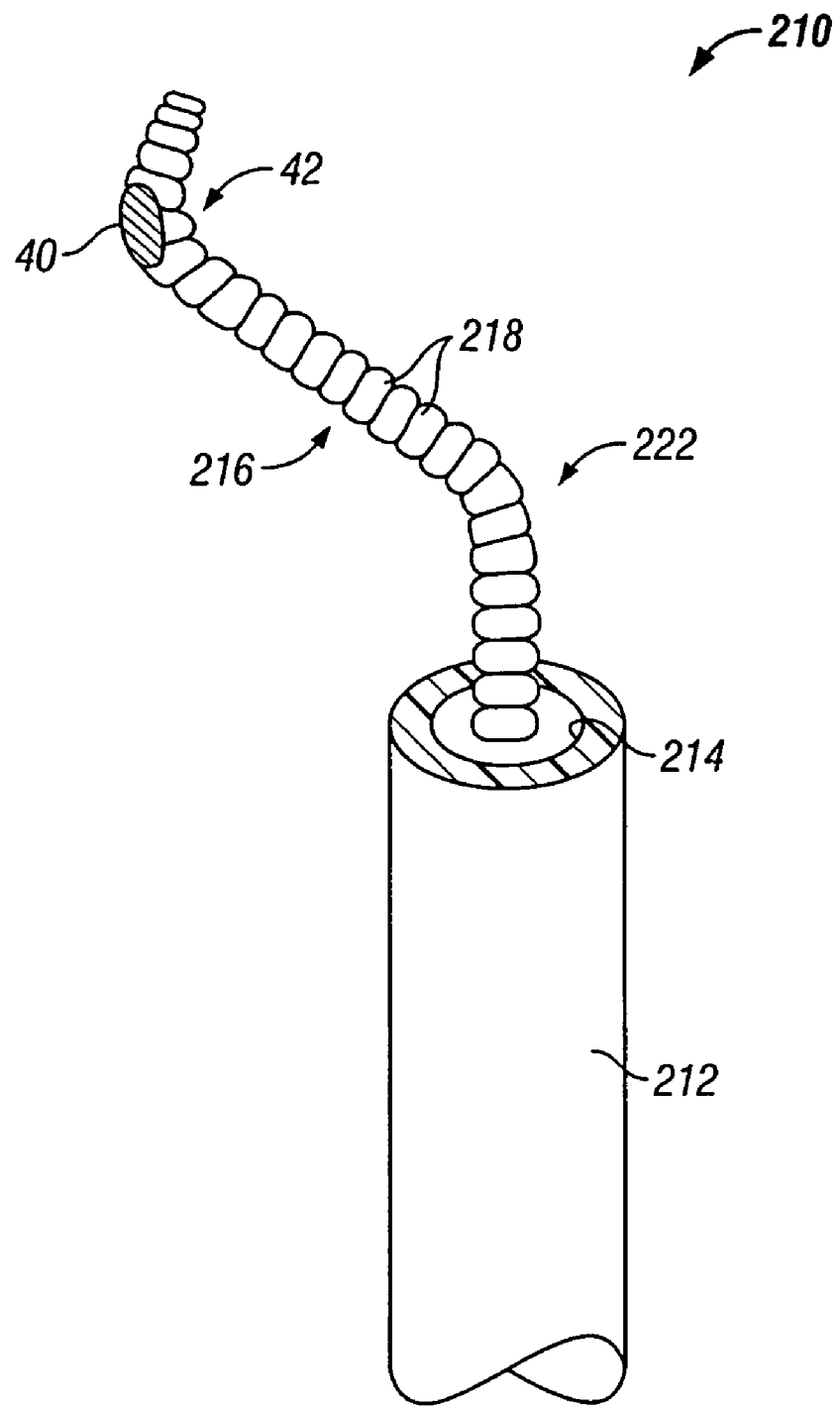
FIG. 4 is a perspective view of yet another preferred embodiment of the present invention.

FIG. 4 shows yet another preferred embodiment of a device 210 for profiling the wall temperature of a hollow body organ. Device 210 can be deployed in a hollow body organ in the manner described above with respect to the embodiments of devices 10 and 10' shown in FIGS. 1, 2 and 3 and described above. Components of device 210 that are similar in structure and function to corresponding components of device 10 of FIGS. 1 and 2 are designated by like reference numerals in the 200 series but having the same last two digits. The description of device 10 above applies also to device 210 unless described otherwise below.

Device 210 of FIG. 4 includes one thermal sensor 40 disposed at the outside of a dogleg bend 42 that is spaced distally from bend 222 and proximally from the terminal end of guidewire 216. Thermal sensor 40 is exposed for contact with the inner wall 228 of vessel 226. An electrical conductor (not shown) is electrically insulated from the wire 218 of guidewire 216 so that guidewire 216 comprises one conductor and the electrical conductor comprises another conductor of the thermocouple or thermistor of thermal sensor 40 for conveying signals from the thermal sensor 40 to the proximal end of guidewire 216 for connection to appropriate signal processing apparatus that converts the signals to a temperature indication. Unlike the embodiments of devices 10 and 10' of FIGS. 1, 2 and 3, device 210 includes only a thermistor at dog-leg bend 42 and no thermistor at the terminal end of guidewire 216 or at bend 222.

Device 210 of FIG. 4 can be used in a manner substantially similar to the manner of use described above with respect to device 10 of FIGS. 1 and 2.

Figure 5:
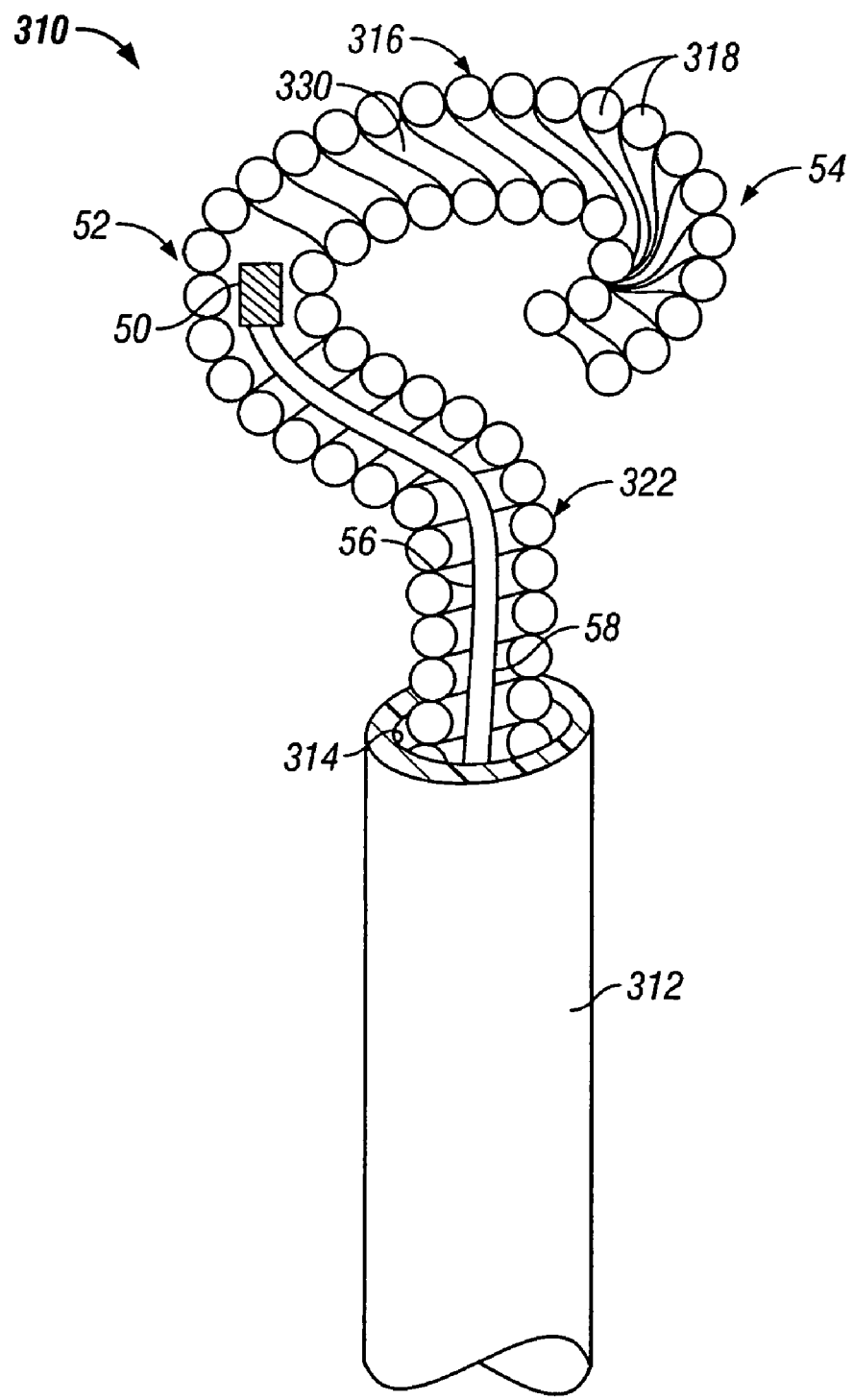
FIG. 5 is a perspective view, partially in section, of a further preferred embodiment of the present invention.

FIG. 5 shows a further preferred embodiment of a device 310 for profiling the wall temperature of a hollow body organ. Device 310 can be deployed in a hollow body organ in the manner described above with respect to the embodiments of device 10 shown in FIGS. 1 and 2 and described above. Components of device 310 that are similar in structure and function to corresponding components of device 10 of FIGS. 1 and 2 are designated by like reference numerals in the 300 series but having the same last two digits. The description of device 10 above applies also to device 310 unless described otherwise below.

Device 310 of FIG. 5, rather than having externally exposed thermal sensors as in the embodiments of FIGS. 1 through 4 above, includes a thermal sensor 50 disposed within the lumen 330 of hollow guidewire 316 and in thermal contact with the coiled wire 318 that comprises guidewire 316. Thermal sensor 50 is located at a dogleg bend 52 that is spaced between bend 322 and the distal end of guidewire 316. Guidewire 316 also includes bend 54 between bend 52 and the distal end of guidewire 316. Bends 322, 52 and 54 together cause the distal portion of guidewire 316 to assume the shape of a question mark when in a relaxed configuration. In such a configuration, bend 52 and bend 54 contact opposite sides of the inner wall of the hollow body organ. The spring nature of guidewire 316 urges bend 52 in contact with the hollow body organ. Insulated electrical conductors 56 and 58 are operatively connected to the thermocouple or thermistor of thermal sensor 50 for conveying signals from the thermal sensor 50 to the proximal end of guidewire 316 for connection to appropriate signal processing apparatus that converts the signals to a temperature indication.

Device 310 of FIG. 5 can be used in a manner substantially similar to the manner of use described above with respect to device 10 of FIGS. 1 and 2.

Figure 6:
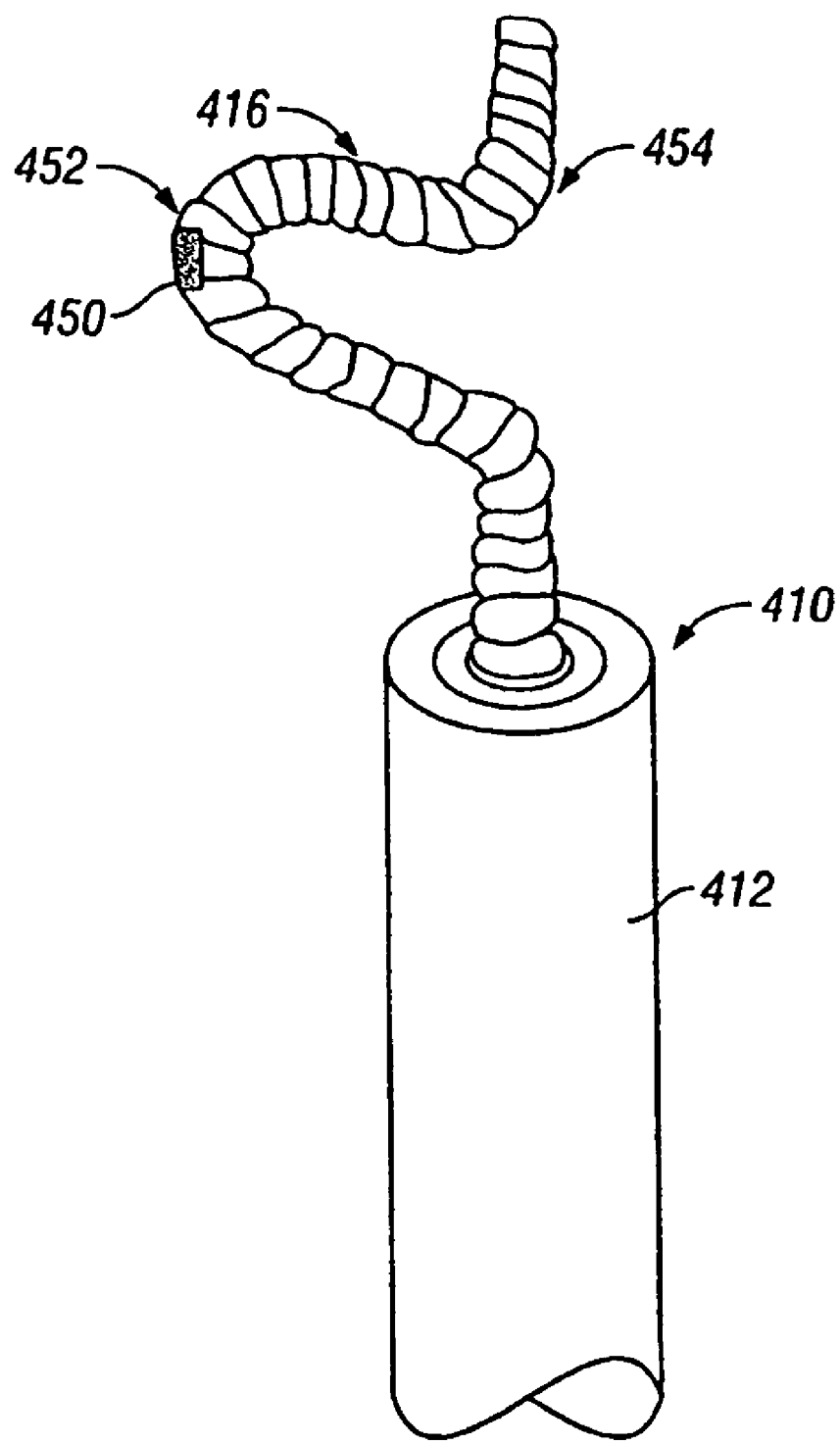
FIG. 6 is a perspective view of yet another preferred embodiment of the present invention.

FIG. 6 shows another embodiment of a device 410 for profiling the wall temperature of a hollow body organ. Device 410 is an alternative configuration of the device 310 of FIG. 5, in which bend 454 extends in a direction opposite to that of bend 54, such that the terminal end portion of guidewire 416 extends axially away from catheter 412. Bend 454 serves a purpose similar to that of bend 54 of device 310 of FIG. 5, i.e., to assure that bend 452, at which thermal sensor 450 is located, remains in contact with the inner wall of the hollow body organ when deployed therein.

Figure 7:
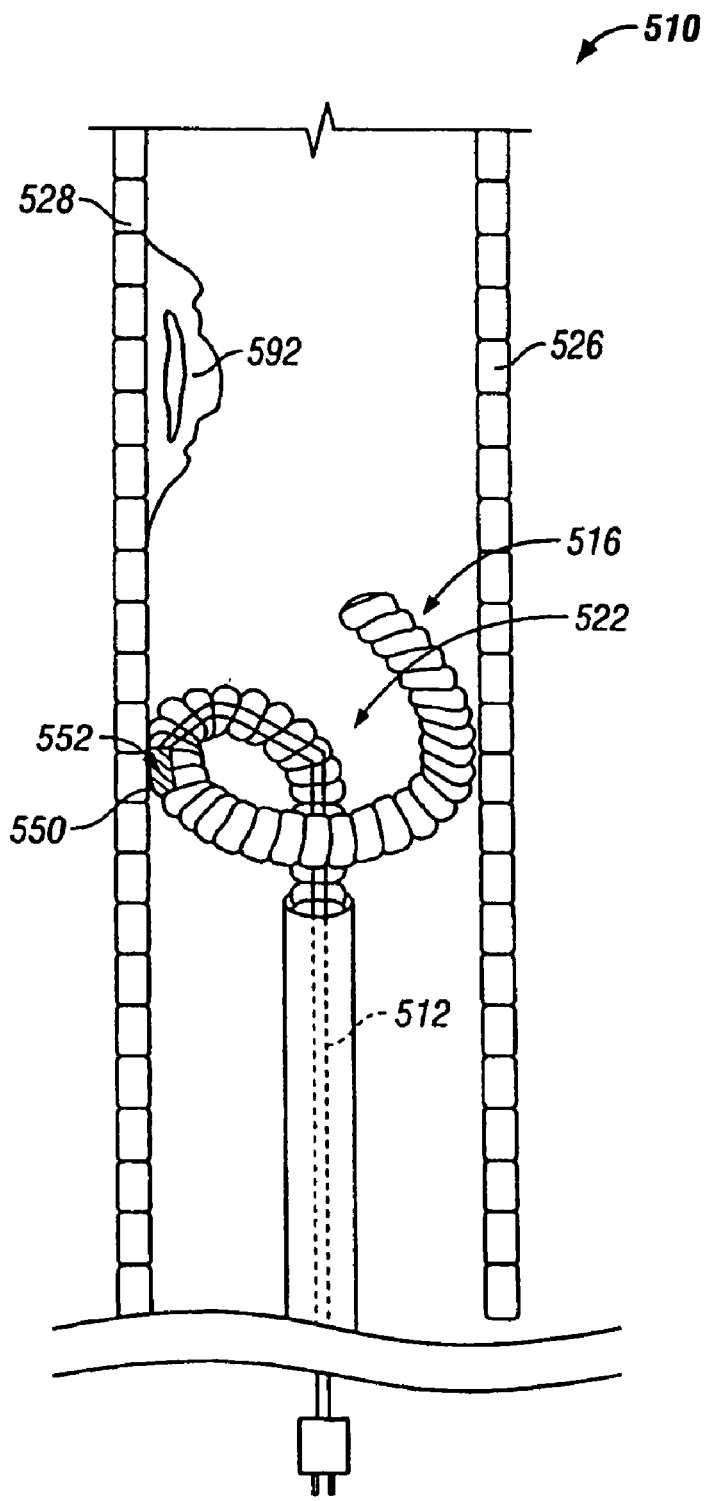
FIG. 7 is a longitudinal sectional view of an arterial hollow body organ in which another preferred embodiment of the present invention, shown in perspective, is deployed.

FIG. 7 shows yet another embodiment of the present invention. Temperature sensing device 510 is carried by hollow guidewire 516 which extends outwardly from the distal end of catheter 512 and includes thermal sensor 550, e.g., a thermistor at a dogleg bend 552 spaced from bend 522 which is situated between the sensor-carrying bend 552 and the distal end portion of catheter 512. The distal end portion of guide wire 516 terminates in a generally crescent-shaped loop and is rotatable, continuously or continually, as desired, to sense the temperature of the endothelium 528 lining the wall of blood vessel 526 in the vicinity of plaque deposit 592.

Figure 8:
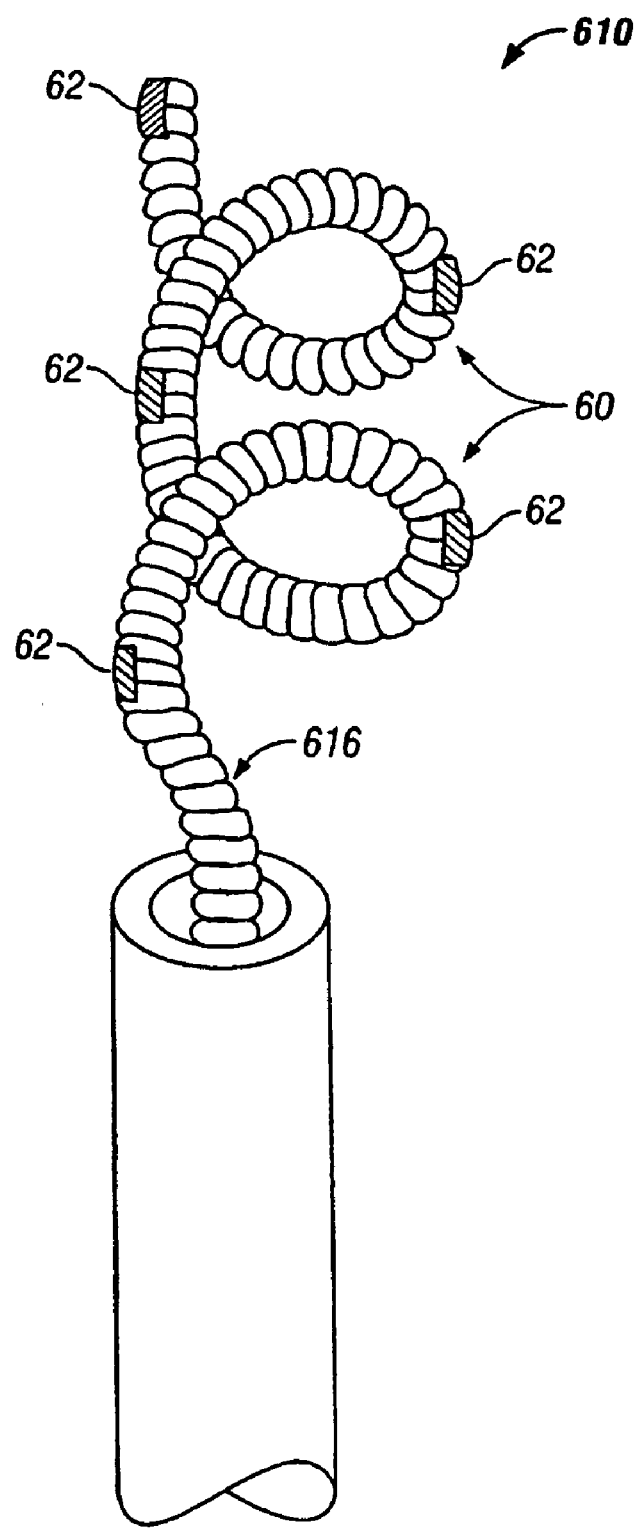
FIG. 8 is a perspective view of a further preferred embodiment of the present invention.

FIG. 8 shows yet a further embodiment of a device 610 for profiling the wall temperature of a hollow body organ. Device 610 comprises another alternative configuration of the device 310 of FIG. 5, in which guidewire 616 is shaped as a plurality of loops 60 with a plurality of thermal sensors 62 located within guidewire 616 at each location along the loops 60 that would contact the wall of the hollow body organ when disposed therein.

Figure 9:
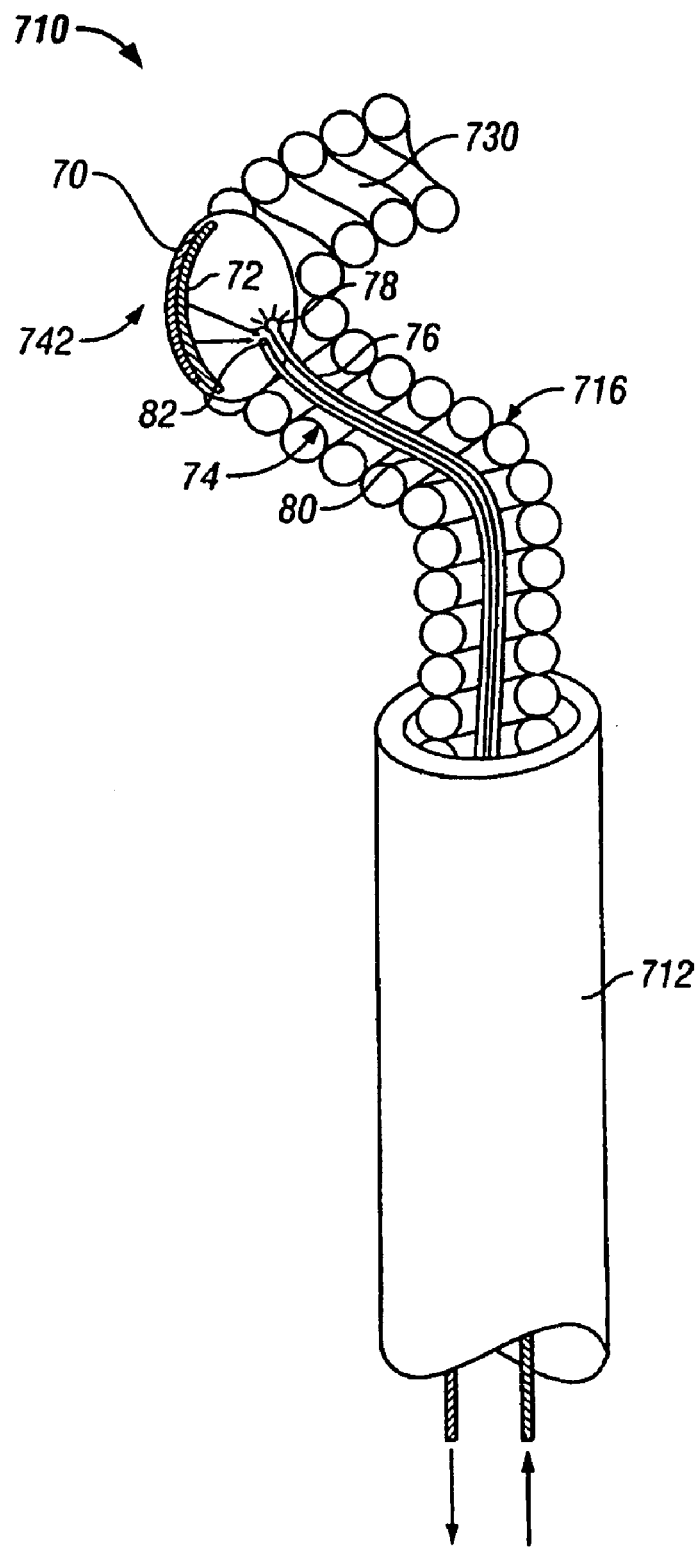
FIG. 9 is a perspective view of another preferred embodiment of the present invention.

FIG. 9 shows yet another embodiment of a device 710 for profiling the wall temperature of a hollow body organ. Device 710 includes a lumened catheter 712 and a hollow guidewire 716. The inner surface of lumen 730 of guidewire 716, at a bend 742 similar to bend 42 of device 210 of FIG. 4, is lined with a layer of black paint 70 which is in turn lined with a thermochromic material 72 that is sensitive to a change of temperature of the guidewire 716. The color of the thermochromic material 72 varies as a function of temperature.

Disposed within lumen 730 of guidewire 716, inwardly of thermochromic material 72, is an optical probe 74 including an illuminating optical fiber 76 having a radially emitting diffuser 78 at the distal end thereof, and a sensing optical fiber 80 having a conically beveled distal end 82 for collecting light. An illuminating electromagnetic radiation source connected to the proximal end of illuminating optical fiber 76 provides illuminating radiation that is guided by optical fiber 76 to the region of interest within the hollow body organ, and diffused radially by diffuser 78 to illuminate the interior of lumen 730, particularly thermochromic material 72. The illuminating radiation can be in the visible, infrared or ultraviolet portions of the spectrum. Radiation from diffuser 78 is differentially absorbed and reflected by thermochromic material 72, according to the color of material 72 which is indicative of the temperature of guidewire 716 in contact with the wall of the hollow body organ in the region of interest.

The light reflected from thermochromic material 72, having wavelengths indicative of the color thereof, is collected by distal end 82 and directed toward the proximal end of sensing optical fiber 80. An appropriate optical reflectance spectrometry device connected to the proximal end of sensing optical fiber 80 generates an electrical signal indicative of the color, and therefore temperature, of thermochromic material 72.

Figure 10:
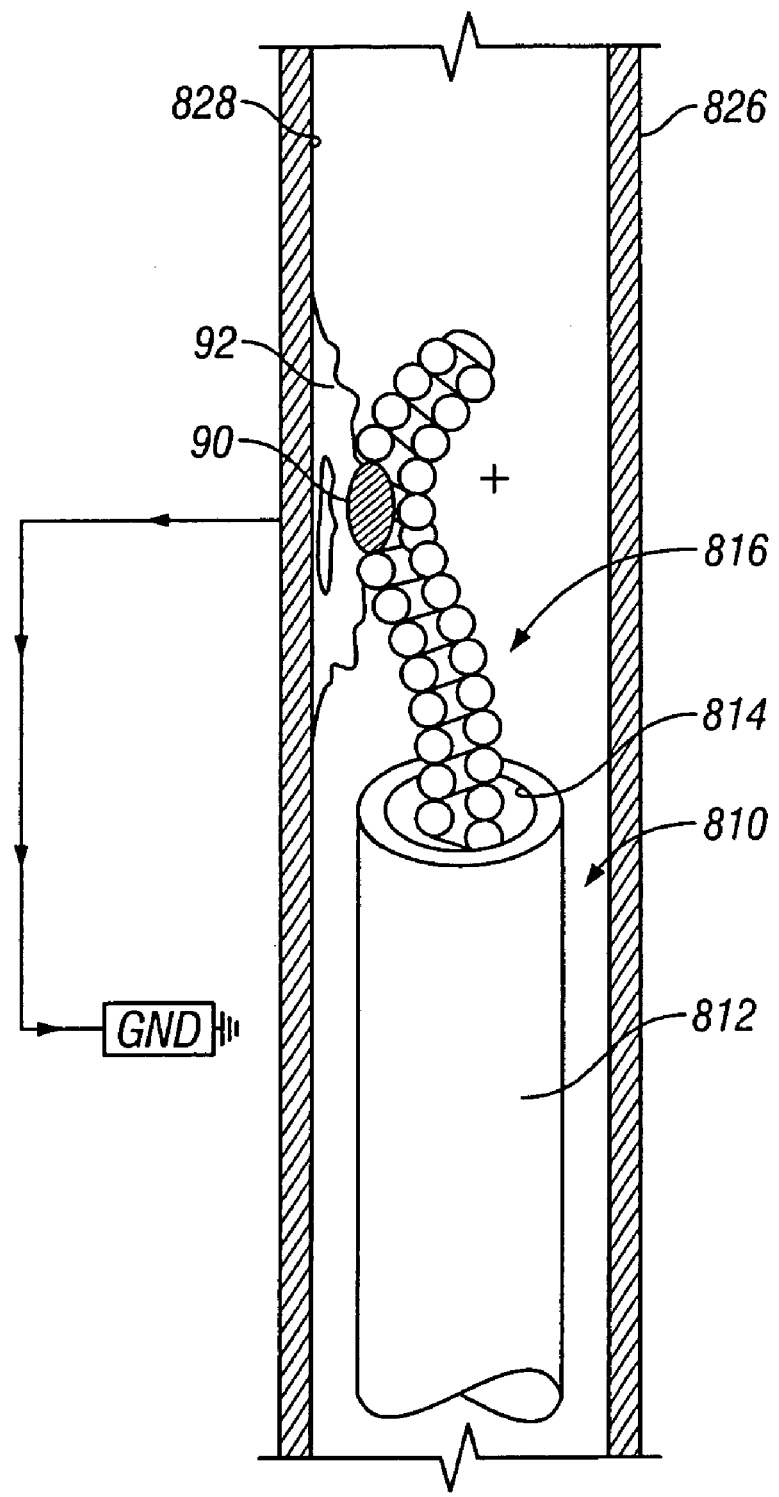
FIG. 10 is a longitudinal sectional view of an arterial hollow body organ in which yet another preferred embodiment of the present invention, shown in perspective, is deployed.

FIG. 10 shows yet another embodiment of a device 810 suitable for profiling the impedance of the wall of a hollow body organ. Device 810 includes a catheter 812 within which is disposed a guidewire 816 having a dog-leg bend in the distal portion thereof. Device 810 is similar in configuration to the embodiment of device 210 of FIG. 4, and like components are indicated by like reference numerals in the 800 series but having the same last two digits. Unlike device 210 of FIG. 4, device 810 does not employ thermal sensing, but rather employs impedance sensing for profiling the wall of a hollow body organ. An electrode 90 at the outside of the dog-leg bend of guidewire 816 is in electrical contact with guidewire 816 and in electrical contact with the inner wall 828 of the hollow body organ 826. Guidewire 816 comprises a conductor operatively connected to an external impedance measuring device that has a ground terminal electrically connected to the body in which the hollow body organ is located. A small electrical current is applied via guidewire 816 and electrode 90 to the inner wall 828 at the region of contact therebetween. The impedance of the electrical path through the body, including through the region of interest in the hollow body organ 826, can be measured and recorded. By moving guidewire 816 relative to the hollow body organ 826 as described above with respect to other embodiments, the impedance of the wall of the vessel 826 can be mapped. Any change of impedance along the wall 828 indicates the presence of an anomaly in the wall, such as a plaque 92.

Although the present invention has been described in detail in terms of preferred embodiments, no limitation on the scope of the invention is intended. The scope of the subject matter in which an exclusive right is claimed is defined in the appended claims.

I claim:

1. A device for sensing a temperature profile of a hollow body organ, comprising:
    a guidewire having a tubular helix structure continuous along an entire length of the guidewire, and sized for intravascular insertion and adapted to be disposed in a relaxed configuration externally of a catheter where a distal tip of the guidewire is laterally displaced relative to a longitudinal axis of the guidewire, and in a contracted configuration internally of the catheter; and
    a temperature sensor connected to the distal tip of the guidewire and moveable therewith, the temperature sensor being adapted to be displaced laterally with the guidewire when in the relaxed configuration, wherein the temperature sensor is further adapted to be rotated about the longitudinal axis via the guidewire.

2. The device of claim 1, wherein the guidewire comprises a material having martensitic transformation properties.

3. The device of claim 2, wherein the guidewire comprises Nitinol.

4. The device of claim 1, wherein the guidewire comprises an elastic material.

5. The device of claim 4, wherein the guidewire comprises spring steel.

6. The device of claim 1, wherein the temperature sensor is a thermocouple.

7. The device of claim 6, wherein the temperature sensor comprises one leg of the thermocouple and the guidewire comprises another leg of the thermocouple.

8. The device of claim 1, wherein the temperature sensor is a thermistor.

9. The device of claim 1, wherein the temperature sensor comprises a thermochromic material.

10. The device of claim 9, wherein the thermochromic material is in thermal contact with a lumen of the guidewire.

11. The device of claim 10, wherein the temperature sensor further includes an optical probe for sensing a color of the thermochromic material.

12. The device of claim 11, wherein the optical probe includes an illumination device for illuminating a region of interest of the guidewire.

13. The device of claim 12, wherein the optical probe includes a sensing device for sensing reflected radiation from the thermochromic material.

14. The device of claim 13, wherein the reflected radiation is in the visible spectrum.

15. The device of claim 13, wherein the reflected radiation is in the infrared spectrum.

16. The device of claim 13, wherein the reflected radiation is in the ultraviolet spectrum.

17. The device of claim 1, wherein the temperature sensor is adapted for rotational displacement about the longitudinal axis of the catheter while in contact with the body organ.

18. The device of claim 1, further comprising a catheter having a longitudinal axis within which the guidewire is disposed.

19. A device for sensing an impedance profile of a body organ, comprising:
    a catheter having a longitudinal axis;
    a guidewire having a tubular helix structure continuous along an entire length of the guidewire, and sized for intravascular insertion and being adapted to be disposed in a relaxed configuration externally of the catheter where a distal tip of the guidewire is laterally displaced relative to a longitudinal axis of the guidewire, and in a contracted configuration internally of the catheter; and
    an electrode connected to the distal tip of the guidewire and moveable therewith, the electrode being adapted to be displaced laterally with the guidewire when in the relaxed configuration, wherein the electrode is further adapted to be rotated about the longitudinal axis via the guidewire.

20. A method for sensing a temperature profile of a hollow body organ, comprising the steps of:
providing a guidewire having a tubular helix structure which is adapted to be disposed in a relaxed configuration externally of a catheter where a distal tip of the guidewire is laterally displaced relative to a longitudinal axis of the guidewire, and in a contracted configuration internally of the catheter;
providing at least one thermal sensor connected to the distal tip of the guidewire and moveable therewith, the at least one thermal sensor being adapted to be displaced laterally with the guidewire when in the relaxed configuration;
advancing the guidewire to a region of interest in a hollow body organ;
relaxing the guidewire within the hollow body organ such that the at least one thermal sensor is displaced laterally in contact with the hollow body organ; and
rotating the at least one thermal sensor about the longitudinal axis.

21. The method of claim 20, wherein the guidewire comprises a material having martensitic transformation properties.

22. The method of claim 21, wherein the guidewire comprises Nitinol.

23. The method of claim 20, wherein the guidewire comprises an elastic material.

24. The method of claim 23, wherein the guidewire comprises spring steel.

25. The method of claim 20, wherein the at least one thermal sensor comprises a thermocouple.

26. The method of claim 25, wherein the at least one thermal sensor comprises one leg of the thermocouple and the guidewire comprises another leg of the thermocouple.

27. The method of claim 20, wherein the at least one thermal sensor comprises a thermistor.

28. The method of claim 20, wherein the at least one thermal sensor comprises a thermochromic material.

29. The method of claim 28, wherein the thermochromic material is in thermal contact with a lumen of the guidewire.

30. The method of claim 29, wherein the at least one thermal sensor further includes an optical probe for sensing a color of the thermochromic material.

31. The method of claim 30, wherein the optical probe includes an illumination device for illuminating a region of interest of the guidewire.

32. The method of claim 31, wherein the optical probe includes a sensing device for sensing reflected radiation from the thermochromic material.

33. The method of claim 32, wherein the reflected radiation is in the visible spectrum.

34. The method of claim 32, wherein the reflected radiation is in the infrared spectrum.

35. The method of claim 32, wherein the reflected radiation is in the ultraviolet spectrum.

36. The method of claim 20, further comprising sensing the temperature of the hollow body organ while rotating the at least one thermal sensor.

37. The method of claim 20, wherein the rotation is continuous.

38. The method of claim 20, wherein the rotation is continual.

39. The method of claim 20, further comprising providing a catheter within which the guidewire is disposed prior to advancing the guidewire to the region of interest.

40. The method of claim 39, further comprising contracting the guidewire elastically and constraining the guidewire within the lumen of the catheter prior to advancing the guidewire to the region of interest.

41. The method of claim 40, further comprising withdrawing the catheter while securing the guidewire against substantial longitudinal movement relative to the hollow body organ, whereby the guidewire relaxes prior to sensing the temperature of the hollow body organ.

* * * * *